United States Patent
Larkin et al.

(10) Patent No.: US 10,537,397 B2
(45) Date of Patent: Jan. 21, 2020

(54) ARM WITH A COMBINED SHAPE AND FORCE SENSOR

(71) Applicant: INTUITIVE SURGICAL OPERATIONS, INC., Sunnyvale, CA (US)

(72) Inventors: David Q. Larkin, Menlo Park, CA (US); Vincent Duindam, San Francisco, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 16/234,227

(22) Filed: Dec. 27, 2018

(65) Prior Publication Data
US 2019/0151034 A1 May 23, 2019

Related U.S. Application Data

(60) Continuation of application No. 16/139,451, filed on Sep. 24, 2018, which is a continuation of application
(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/77* (2016.02); *B25J 9/1689* (2013.01); *B25J 13/025* (2013.01);
(Continued)

(58) Field of Classification Search
CPC ............ A61B 19/2203; A61B 19/5212; A61B 19/5244; A61B 2017/00057;
(Continued)

(56) References Cited

U.S. PATENT DOCUMENTS 5,807,377 A 9/1998 Madhani et al.
6,424,885 B1 7/2002 Niemeyer et al.
(Continued)

OTHER PUBLICATIONS

Askins, Charles G. et al., "Bend and Twist Sensing in a Multi-Core Optical Fiber," Optical Fiber Communications/National Fiber Optic Engineers conference, 2008 (OFC/NFOEC 2008), Feb. 24-28, 2008, San Diego, CA, pp. 1-3, IEEE.
(Continued)

*Primary Examiner* — Bao Long T Nguyen
(74) *Attorney, Agent, or Firm* — Haynes and Boone, LLP

(57) ABSTRACT

A robotic surgical system comprising a surgical instrument. The surgical instrument includes an elongate, hollow shaft having a proximal end, a distal end, and a flexible section. The surgical instrument also includes a sensor apparatus comprising an electromagnetic sensor. The robotic surgical system also includes a force transmission mechanism coupled to the proximal end of the shaft and a processor communicatively coupled to at least the sensor apparatus. The processor is configured to receive sensor data from the sensor apparatus and to use the sensor data with mechanical property data for the surgical instrument and material property data for the surgical instrument to determine external force information for the surgical instrument.

21 Claims, 4 Drawing Sheets

Related U.S. Application Data

No. 15/345,029, filed on Nov. 7, 2016, now Pat. No. 10,105,188, which is a continuation of application No. 14/560,501, filed on Dec. 4, 2014, now Pat. No. 9,500,548, which is a division of application No. 12/490,487, filed on Jun. 24, 2009, now Pat. No. 8,918,212.

(51) Int. Cl.
```
G01L 5/22      (2006.01)
B25J 18/06     (2006.01)
B25J 13/02     (2006.01)
B25J 9/16      (2006.01)
```

(52) U.S. Cl.
CPC ............... *B25J 18/06* (2013.01); *G01L 5/226* (2013.01); *A61B 2034/301* (2016.02); *Y10S 901/15* (2013.01); *Y10S 901/17* (2013.01); *Y10S 901/46* (2013.01)

(58) Field of Classification Search
CPC .. A61B 2017/2906; A61B 2017/00477; A61B 2019/2234; A61B 2019/2242; A61B 2019/5248; A61B 2019/5259; A61B 2019/5261; A61B 2019/2223; A61B 34/30; A61B 34/77; A61B 2034/301; G01L 5/226; B25J 18/06; B25J 9/1689; B25J 13/025; Y10S 901/15; Y10S 901/46; Y10S 901/17
USPC ............. 901/14–15, 27–29, 46, 17; 700/258, 700/260–261; 600/141, 145–146; 606/15–16, 19
See application file for complete search history.

(56) References Cited

U.S. PATENT DOCUMENTS

| | | | |
|---|---|---|---|
| 6,461,372 B1 | 10/2002 | Jensen et al. | |
| 6,730,021 B2 | 5/2004 | Vassiliades, Jr. et al. | |
| 6,817,974 B2 | 11/2004 | Cooper et al. | |
| 6,999,852 B2 | 2/2006 | Green | |
| 7,607,540 B2 | 10/2009 | Ballard | |
| 7,720,322 B2 | 5/2010 | Prisco | |
| 7,752,920 B2 | 7/2010 | Larkin et al. | |
| 7,843,158 B2 | 11/2010 | Prisco et al. | |
| 7,988,215 B2 | 8/2011 | Seibold | |
| 8,918,212 B2 | 12/2014 | Larkin et al. | |
| 9,186,046 B2* | 11/2015 | Ramamurthy | A61B 5/06 |
| 9,500,548 B2 | 11/2016 | Larkin et al. | |
| 9,895,813 B2 | 2/2018 | Blumenkranz et al. | |
| 10,105,188 B2 | 10/2018 | Larkin et al. | |
| 2005/0200324 A1 | 9/2005 | Guthart et al. | |
| 2007/0151390 A1 | 7/2007 | Blumenkranz et al. | |
| 2007/0156019 A1* | 7/2007 | Larkin | B25J 19/025 600/104 |
| 2007/0197939 A1 | 8/2007 | Wallace et al. | |
| 2007/0233044 A1 | 10/2007 | Wallace et al. | |
| 2008/0009750 A1 | 1/2008 | Aeby et al. | |
| 2008/0065111 A1 | 3/2008 | Blumenkranz et al. | |
| 2008/0255505 A1 | 10/2008 | Carlson et al. | |
| 2008/0275367 A1* | 11/2008 | Barbagli | G16H 40/63 600/587 |
| 2009/0038413 A1 | 2/2009 | Seibold et al. | |
| 2009/0076476 A1 | 3/2009 | Barbagli et al. | |
| 2009/0088634 A1 | 4/2009 | Zhao et al. | |
| 2009/0088773 A1 | 4/2009 | Zhao et al. | |
| 2009/0088897 A1 | 4/2009 | Zhao et al. | |
| 2009/0157092 A1 | 6/2009 | Blumenkranz et al. | |
| 2009/0192522 A1 | 7/2009 | Blumenkranz | |
| 2009/0248038 A1 | 10/2009 | Blumenkranz et al. | |
| 2009/0254083 A1 | 10/2009 | Wallace et al. | |
| 2010/0121138 A1 | 5/2010 | Goldenberg et al. | |
| 2010/0168918 A1 | 7/2010 | Zhao et al. | |
| 2010/0169815 A1 | 7/2010 | Zhao et al. | |
| 2010/0298844 A1 | 11/2010 | Blumenkranz | |

OTHER PUBLICATIONS

Calvert, Sean, "High speed dual-axis strain using a single fiber Bragg grating," 2004, 12 pages, SPIE, vol. 5384, http://www.bluerr.com/papers/BRR-2004_SPIE_Vol5384_p229.pdf.

Culshaw B., "The optical fibre Sagnac interferometer: an overview of its principles and applications," Measurement Science and Technology, 2006, pp. R1-R16, vol. 17, Institute of Physics Publishing.

Dakin, John P. and Mark Volanthen, "Distributed and Multiplexed Fibre Grating Sensors, Including Discussion of Problem Areas," IEICE Transactions on Electronics, vol. E83-C, No. 3, Mar. 2000, pp. 391-399.

Duncan, Roger, "Sensing Shape: Fiber-Bragg-grating sensor arrays monitor shape at a high resolution," 2005, pp. 18-21, SPIE.

Endosense, "Endosense Product Overview," 2 pages, http://www.endosense.com/professionsal/product-overview.html (last visited Aug. 25, 2011).

Jin, Long et al., "Two-dimensional bend sensing with a cantilever-mounted FBG [Fiber Bragg Grating]," Meas. Sci. Technol., 2006, pp. 168-172, vol. 17, Institute of Physics Publishing.

Kunzler, Marley et al., "Use of Multidimensional Fiber Grating Strain Sensors for Damage Detection in Composite Pressure Vessels," Proceedings of SPIE, vol. 5758, p. 83 (10 pages), 2005.

Lowder, Tyson L. et al., "Multi-Axis Bend Sensing Using a Single Surface Relief Fiber Bragg Grating," Optical Society of America, 2006, 4 Pages.

Lunwei Z., et al., "FBG Sensor Devices for Spatial Shape Detection of Intelligent Colonoscope," IEEE International Conference on Robotics and Automation, Apr. 2004, New Orleans, Louisiana, pp. 835-840.

Martinez, A. et al., "Vector Bending Sensors Based on Fibre Bragg Gratings Inscribed by Infrared Femtosecond Laser," Electronics Letters, 2005, pp. 472-474, vol. 41—Issue 8.

Passy, R. et al., "Experimental and Theoretical Investigations of Coherent OFDR with Semiconductor Laser Sources," Journal of Lightwave Technology, vol. 12, No. 9, Sep. 1994, pp. 1622-1630.

Passy, R. et al., "High-Sensitivity-Coherent Optical Frequency-Domain Reflectometry for Characterization of Fiber-optic Network Components," IEEE Photonics Technology Letters, vol. 7, No. 6, Jun. 6, 1995, pp. 667-669.

Peirs, Jan et al., "A micro optical force sensor for force feedback during minimally invasive robotic surgery," Sensors and Actuators A, 2004, pp. 447-455, vol. 115.

Rice, Trevor et al., "Fiber Optic Distributed Strain, Acoustic Emission, and Moisture Detection Sensors for Health Maintenance," Proceedings of the IEEE Systems Readiness Technology Conference, Sep. 22-25, 2003 (Autotestcon 2003), pp. 505-514.

Soller, Brian J. et al., "High resolution optical frequency domain reflectometry for characterization of components and assemblies," Optics Express, Jan. 24, 2005, vol. 13, Issue 2, pp. 666-674.

Soller, Brian J. et al., "Optical Frequency Domain Reflectometry for Single- and Multi-mode Avionics Fiber-Optics Applications," Proceedings of IEEE Conference on Avionics and Photonics, 2006, pp. 38-39, IEEE.

Spring.pdf, Douglas Wright, DA Notes: Springs: Introduction, URL:<http://www.ejsong.com/mdme/memmods/MEM30009A/lifting_systems/Univ_of_WA.htm>, Aug. 2005, pp. 1-8.

Tunay, Ilker, "Position control of catheters using magnetic fields," Proc. IEEE International Conference on Mechatronics, 2004, pp. 392-397, IEEE.

Udd, Eric et al., "Three Axis Strain and Temperature Fiber Optic Grating Sensor," Proceedings of SPIE, conference on Feb. 26, 1996, Sand Diego, CA, vol. 2718, p. 104, (1996) SPIE.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

(56) References Cited

OTHER PUBLICATIONS

Wang, Yi-Ping et al., "A novel long period fiber grating sensor measuring curvature and determining bend-direction simultaneously," IEEE Sensors Journal, 2005, pp. 839-843, vol. 5—Issue: 5, IEEE.

Wong, Allan C. L. et al., "Multiplexed fibre Fizeau interferometer and fibre Bragg grating sensor system for simultaneous measurement of quasi-static strain and temperature using discrete wavelet transform," Measurement Science and Technology, vol. 17, 2006, pp. 384-392.

* cited by examiner

ARM WITH A COMBINED SHAPE AND FORCE SENSOR

CROSS-REFERENCE TO RELATED APPLICATIONS

This application is a Continuation of U.S. patent application Ser. No. 16/139,451, filed Sep. 24, 2018, which is a Continuation of U.S. patent application Ser. No. 15/345,029, filed Nov. 7, 2016, which is a Continuation of U.S. patent application Ser. No. 14/560,501, filed Dec. 4, 2014, which is a Divisional of U.S. patent application Ser. No. 12/490,487, filed Jun. 24, 2009, the full disclosures of which (including all references incorporated by reference therein) are incorporated herein by reference in their entirety for all purposes.

BACKGROUND

1. Field of Invention

Aspects of the invention relate to a system for using a sensor to monitor both the shape of an arm as well as an external force applied to that arm. Some aspects of the invention are particularly suited for monitoring flexible guide tubes and articulated arms used in robotic surgery.

2. Art

There has been considerable effort in developing systems for performing minimally invasive surgery. One area of particular interest is robotically assisted surgery.

In robotically assisted surgery, the surgeon typically operates a control device at a location that is remote from the patient to control the motion of surgical instruments at the patient's surgical site. The control device typically includes one or more manually operated input devices, such as multiple degree of freedom master tool manipulators, joysticks, exoskeletal gloves, or the like, which are coupled to the surgical instruments via servo motors for articulating the instruments at the surgical site. During the surgical operation, the control device controls a surgical robotic manipulator that provides mechanical articulation and functional control of a variety of surgical instruments, such as tissue graspers, needle drivers, electrosurgical cautery probes, etc., that each perform various functions for the surgeon, e.g., holding or driving a needle, grasping a blood vessel, dissecting, cauterizing, or coagulating tissue.

Such systems typically include at least one arm having a plurality of joints that interconnect small links to provide articulation. Some form of control mechanism is provided to move the arm into various poses. For example, the control mechanism can include one or more tendons (e.g., cables) running along the length of the arm. Tensioning one or more of the tendons causes the arm to bend at the joints. The tendons may actively control the arm's bending and straightening. Alternatively, in some designs, each joint can be provided with a stiffening element (e.g., a spring) that provides a restoring force to return the arm to a straight orientation when tension on a tendon has been relaxed. Some practical designs may contain multiple bending links per joint. In such multiple-link joints, the stiffening element controls how the multiple bending links bend in a coordinated fashion to form the complete joint.

Although there is a direct relationship between the amount of tension placed on the tendons and the resulting shape of the arm, mechanical tolerances, drive train friction, tendon stretch, and other conditions may prevent one from determining the actual shape of the arm with sufficient precision if the determination is based solely on cable tension. Therefore, various efforts have been made to develop a system to continuously monitor the actual shape of the arm as it moves during a surgical procedure.

One such monitoring approach is disclosed in U.S. Patent Application Pub. No. US 2007/0156019 A1 (filed Jul. 20, 2006) (the "'019 Application"), which is incorporated herein by reference. This approach relies on a fiber optic shape sensor. In this type of device, an optical fiber is provided with a plurality of cores. Arrays of Bragg gratings are formed along the core continuously or at spaced-apart locations. Each Bragg grating comprises a series of modulations of the core's refractive index so as to generate a spatial periodicity in the refraction index. The spacing may be chosen so that the partial reflections from each index change add coherently for a narrow band of wavelengths, and therefore they reflect only this narrow band of wavelengths while passing a much broader band. During fabrication of the gratings, the modulations are spaced by a known distance, thereby causing reflection of a known band of wavelengths. When a strain is induced on the fiber core, the spacing of the modulations will change, depending on the amount of strain in the core.

To measure strain, light is sent down the fiber, and the reflected wavelength is a function of the strain on the fiber and its temperature. This fiber Bragg grating (FBG) technology is commercially available from a variety of sources, such as Smart Fibres Ltd. of Bracknell, England. When applied to a multicore fiber, bending of the optical fiber induces strain on the cores that can be measured by monitoring the wavelength shifts in each core. By having two or more cores disposed off-axis (i.e., not coincident with the lengthwise center longitudinal axis) in the fiber, bending of the fiber induces different strains on each of the cores. These strains are a function of the local degree of bending of the fiber. Regions of the cores containing FBGs, if located at points where the fiber is bent, can thereby be used to determine the amount of bending at those points.

The collected data, combined with the known spacings of the FBG regions, can be used to reconstruct the shape of the fiber. Such a system has been described by Luna Innovations, Inc. of Blacksburg, Va.

The '019 Application describes how this technology can be used to monitor the shape of a robotic arm. As discussed therein, a control system can be provided for detecting the position of the surgical instrument and for utilizing that information to assist in surgical procedures. In one embodiment, the control system includes a detection system and a servo controller. The detection system is utilized for generating and detecting the light used for determining the position of the instrument. The servo controller may utilize the position information as feedback for positioning the instrument.

When using an articulated arm during surgery, it is also desirable to know about any external forces placed on the arm, particularly external forces applied at the distal tip. Information about the external forces upon the arm can be fed back to the surgeon during the procedure to facilitate the manipulation of the arm.

Various approaches have been developed for monitoring the external forces placed upon an articulated arm. In one example, strain gauges are placed on rigid portions of the arm. External forces induce strain in the gauges that can be measured. Examples of the use of force sensors in robotic arms can be found in the '019 Application, U.S. Patent Application Pub. No. US 2008/0065111 A1 (filed Sep. 29, 2007), U.S. patent application Ser. No. 11/858,772, (filed Dec. 18, 2007), and U.S. patent application Ser. No. 12/060, 004, (filed Mar. 31, 2008), all incorporated herein by reference.

SUMMARY

As noted above, when operating an articulated arm for robotic surgery, it is desirable that both the shape of the arm and external forces acting upon the arm be known. The subject invention is based on the recognition that data generated by bend sensors can also be used, in most circumstances, to derive information about external forces. In particular, the system must be of the type wherein the external force does not influence the shape of the arm in the same direction as the internal actuation or kinematic constraint forces. An example where this condition would be violated is when a force is directed against the tip of a straight arm along the longitudinal axis of the arm. In this situation, (and assuming no measurable compression or buckling occurs) the external force would not affect the shape of the arm and could not be measured. Where the external force causes the shape of the arm to deviate from the shape it would achieve based only on the cable actuation, however, the external force can be determined.

In accordance with an aspect of the invention, an articulated arm is provided with one or more control tendons for changing the shape of the arm. In addition, the arm is provided with a plurality of bend sensors. In a preferred embodiment, the bend sensors are Bragg gratings formed on an optical fiber, as described in the prior art.

In use, the fiber optic bend sensors are interrogated in a manner similar to past ways. In the subject approach, however, data from the interrogation is analyzed to derive both the internal actuation force applied to the arm as wen as the external force acting on the arm.

As discussed below, aspects of the invention are applicable to systems both with and without stiffening elements.

Aspects of the invention are also generally applicable to flexible probes that do not include any internal actuation mechanisms for example, bend sensors can be used with a flexible spring element to monitor the shape of the element in response to an external force. The information from the bend sensors can be used to compute the external force.

DETAILED DESCRIPTION

Figure 1:
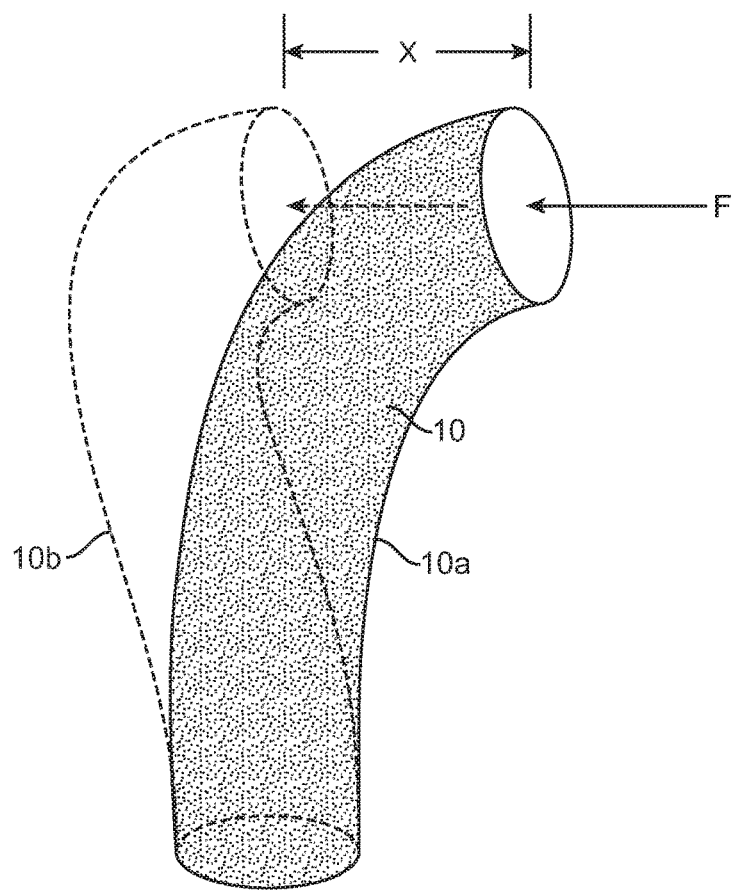
FIG. 1 is a diagrammatic view that illustrates a bask inventive concept.

Arms, including instruments and structures used to support and move such instruments, may be substantially rigid or flexible. Flexible instruments may be classified into two types: (i) continuously flexible arms that do not have discrete joints (i.e., infinite degrees of freedom), and (ii) arms that have a series of two or more short links interconnected by joints having at least one degree of freedom (the number of degrees of freedom being sufficient to provide the required flexibility). Many medical devices, such as catheters and small diameter minimally invasive instruments, have such a continuously flexible property. Many other medical devices, such as relatively large diameter endoscopes that include one or more working channels for minimally invasive instruments, are made of such a series of short, interconnected links. It is possible to have a hybrid flexible arm that includes at least one continuously flexible portion and at least one link portion. Arms with both rigid and flexible (continuous, linked, or hybrid) portions are also possible.

Such arms may be actuated to move by various methods that provide a necessary actuation force. One exemplary method is actuation with one or more tendons (e.g., cables) that run along the length of an arm. A pulling force (tension) in one or more of the tendons bends the arm or a segment in the arm. Actuation force may be provided from various sources, such as manual crank or a servomotor. Other mechanical actuation methods, such as providing pushing force (compression) on tendons, using gears, etc. are known and may be used.

An arm may include a passive stiffening element that applies a restoring force to a default pose for the arm. Stiffening elements may be of various forms, such as an internal spring that runs inside the flexible arm or an external sheath that surrounds the flexible arm. When no bending forces are applied to such an arm, the stiffening element enforces a minimum energy shape or kinematic configuration. If a bending force is applied to the arm, the stiffening element opposes the bending force on the portion of the arm that is being moved.

Both internal actuation force and external force may be applied to the arm. An example of an external force is the reactive force the arm experiences if it is pushed against tissue. The stiffening element opposes both externally applied force and the internal actuation force. In addition to opposing the actuation force, the stiffening element also spreads the actuation force across the bending portion of the arm so that, for instance, the angle between each link in a series of links is about equal.

It is possible to use a bend or shape sensor to detect not just the minimal bends associated with the normal actuation of the arm, but also the perturbation generated by an external force, of the stiffening element away from its minimum energy shape. It is therefore possible to detect the magnitude and direction of the applied external force in addition to the shape of the arm.

The subject invention can be implemented using fiber optic shape sensing technology of the type disclosed in the '019 Application, referenced above. (See also, U.S. patent application Ser. No. 12/164,829, (filed Jun. 30, 2008), which is incorporated by reference.) As discussed below, other shape sensing technologies could be used.

Aspects of the invention may be applied to several arm configurations. One illustrative configuration is to have a non-actuated continuously flexible arm with a stiffening element. A simple example of this first illustrative configuration is the optical fiber bend sensor alone since it is continuously flexible and possesses an inherent stiffness. A second configuration is to have an actuated continuous or discretely flexible arm with a stiffening element. This second configuration, on which much of the following description is based, is underactuated, because actuation does not fully control the shape. A third configuration is to have an actuated discrete link flexible arm without an additional stiffening element. Since the stiffening element is not present in this third configuration, the arm's actuation mechanism must be able to completely determine the arm's kinematic position (i.e., every degree of freedom is actuated). In each of these illustrative configurations, the mechanical properties of these configurations (e.g., dimensions (such as link size, distance between joints, fit tolerances, and the like), material properties (such as known or estimated friction, cable "stretchiness", and the like), etc.) are known so that such information can be combined with information from the sensor to derive the actuation force and/or a force externally applied to the arm.

FIG. 1 illustrates a basic inventive concept. An arm is illustrated as a tubular member 10, which includes an internal stiffening element (not shown). In pose 10a, tubular member 10's curved shape is caused by internal tensioning (actuation) forces. If a force F is applied to the end of the member 10 in pose 10a, it will begin to bend in an "S" like shape as illustrated by pose 10b, since the internal stiffening element must deflect to create a restoring force equal to force F. If a shape sensor is used to measure the bend in member 10, the information it generates can also be used to measure the external force. In FIG. 1, X represents the distance between the arm's minimum energy shape under the internal actuation force and the arm's actual shape (the result of the external force). For stiffness matrix K that may depend upon X, F is the force (F=KX).

Figure 2:
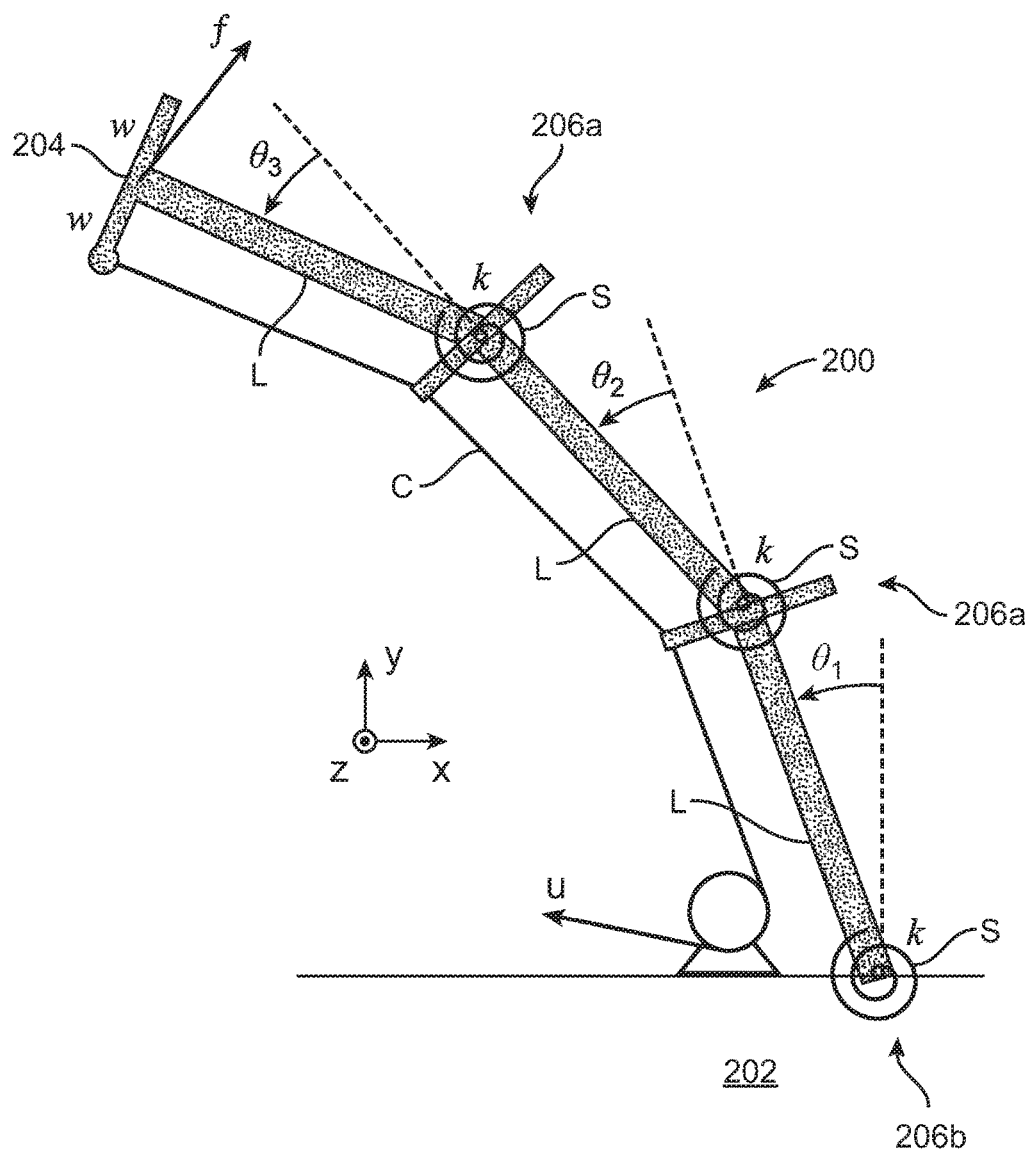
FIG. 2 is a diagrammatic view of elements of an arm and the associated forces that will be calculated in accordance with an aspect of the subject invention.

FIG. 2 provides a more detailed example. In this example, the elongate arm 200 is attached at one end (the proximal end) to a fixed, known position 202. The position of the distal end 204 is determined by a number of forces acting on the arm. First, the arm contains a stiffening element that provides forces that restore the arm to a certain preferred shape. Second, some actuation mechanism (e.g., a servo actuator) actively influences the shape of the arm. Finally, an external force is applied at the distal end 204 of the arm. The total shape of the arm is measured by a sensing apparatus (not shown).

As shown in FIG. 2, the elongate arm 200 is a planar device composed of three rigid links L (links L may be relatively short, to form a flexible configuration that approximates a continuously flexible arm, or they may be relatively longer). Two revolute joints 206a couple the ends of the links L in series, and a third revolute joint 206b couples the proximal end of the arm to base 202. The axes of the revolute joints are parallel, so that the arm articulates in a plane (x-y, as shown). The stiffening element is a combination of three equal torsional springs S, each with stiffness k, that are attached at each joint 206. The actuation mechanism is a single cable C attached at the distal tip 204 and routed along the links, and the sensing apparatus (not shown) measures the angles of the three joints 206. The external force is a linear force in the arm's plane of motion that is applied at the distal tip, as illustrated by the arrow.

The three forces (stiffness, actuation, external) act at different locations and in different ways on the arm, but the forces can be compared by writing a force balance for the torques applied at each of the three joints. For a general arm with n joints, standard robotics theory and geometry are used to make this force balance:

$$0 = \tau = Wu - K\theta + Bf$$

where $\tau$ is the total combined n-dimensional torque vector, which should balance to zero if the system is not moving, u is the c-dimensional vector of cable forces, $\theta$ is the n-dimensional vector of joint angles, and f is the e-dimensional vector of external tip forces. In other words, n is the number of mechanical degrees of freedom, c is the degree of actuation, and e is the number of independent external force directions. For the example in FIG. 2, (n, c, e)=(3, 1, 2), and the matrices W, K, and B are:

$$W = \begin{bmatrix} w\cos(\theta_1) \\ w\cos(\theta_2) \\ w\cos(\theta_3) \end{bmatrix}$$

$$K = \begin{bmatrix} k & 0 & 0 \\ 0 & k & 0 \\ 0 & 0 & k \end{bmatrix}$$

$$B = -l \begin{bmatrix} \cos(\theta_1) + \cos(\theta_1 + \theta_2) + & \sin(\theta_1) + \sin(\theta_1 + \theta_2) + \\ \cos(\theta_1 + \theta_2 + \theta_3) & \sin(\theta_1 + \theta_2 + \theta_3) \\ \cos(\theta_1 + \theta_2) + \cos(\theta_1 + \theta_2 + \theta_3) & \sin(\theta_1 + \theta_2) + \sin(\theta_1 + \theta_2 + \theta_3) \\ \cos(\theta_1 + \theta_2 + \theta_3) & \sin(\theta_1 + \theta_2 + \theta_3) \end{bmatrix}$$

The force balance equation can be used to determine the unknown external forces by f measuring the shape $\theta$ of the arm. The approach assumes that external tip forces influence the shape differently than the (unknown) cable forces u, such that if sufficient shape variables $\theta$ are available (i.e., n is large enough), u and f can be recovered at the same time.

The force balance equation can be used to recover both the external force f and the actuation force u, provided that sufficient shape information is available and the actuation and external forces influence the shape independently. For the example of FIG. 2 and similar tendon-actuated arms, these conditions are met unless the system is at a kinematic singularity.

The force balance can be rewritten, separating the known from the unknown variables, as follows:

$$[W \quad B] \cdot \begin{bmatrix} u \\ f \end{bmatrix} = K\theta$$

If the matrix [W B] has full column rank c+e (this is the mathematical formulation of the condition "independent shape influence"), the unknown variables u and f can be uniquely recovered, for example using a pseudo-inverse as:

$$\begin{bmatrix} u \\ f \end{bmatrix} = [W \quad B]^+ K\theta = \left( \begin{bmatrix} W^T \\ B^T \end{bmatrix} \cdot [W \quad B] \right)^{-1} \begin{bmatrix} W^T \\ B^T \end{bmatrix} K\theta$$

Intuitively, the way the force information is obtained is by comparing the measured shape to a shape that could be achieved using only cable actuation. For example, without external forces, the system in FIG. 2 will acquire a circular shape with all angles $\theta$ equal, and solving the previous equation will return a solution (u, f) with f=0. If $\theta$ describes a shape that is not a circle, then the equation translates this "non-circle" shape to external forces f that must have caused it.

Finally, it is important to note that this derivation relies on the facts that the arm is only partially actuated (c<n), only certain external forces are applied (e<n), and the shape measurement is rich enough to independently describe both effects (c+e≤n). These dimensional relations, plus the condition that the matrix [W B] must have full column rank, can be used to generalize to more complex mechanisms.

It should be understood that the more degrees of freedom of movement in the system, the easier it is to mathematically derive the external forces on the system (the best case, therefore is with the infinite degrees of freedom of a continuously flexible arm). The example above also focused on recovering an external force applied to the distal tip. It should be understood that depending on the structure of the arm, external force(s) applied between the distal and proximal ends could also be determined. And, if sufficient shape information is available an external force component directed along the arm's longitudinal axis can be determined.

Figure 3:
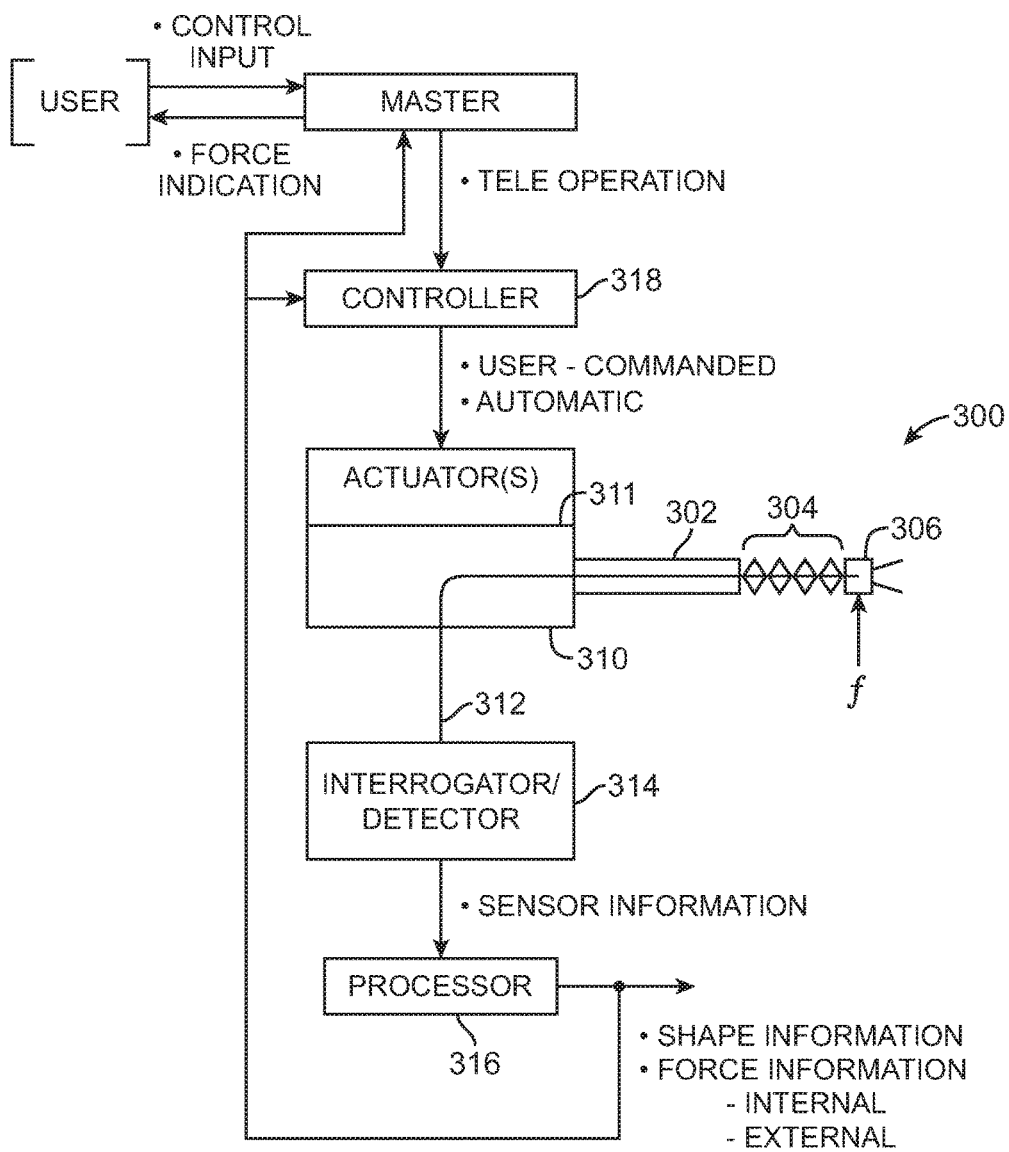
FIG. 3 is diagrammatic view of one embodiment of the subject invention.

FIG. 3 is a schematic diagram of another illustrative embodiment of the subject invention. In this illustration, the arm is a minimally invasive surgical instrument 300 that includes an elongated hollow, substantially rigid shaft 302 coupled at its distal end to a flexible wrist section 304. A surgical end effector 306, such as a tissue grasper, is connected to the distal end of the wrist section. A force transmission mechanism 310 is coupled to the proximal end of the shaft. Teleoperated servomotor actuators engage the transmission mechanism 310 at mechanical interface 311, which in turn passes actuating forces through shaft 302 via cables (not shown) to cause the wrist section mechanism to bend in pitch and/or yaw and to actuate the end effector. (See U.S. Pat. No. 6,817,974 (filed Jun. 28, 2002), U.S. Pat. No. 5,807,377 (filed May 16, 1997), and U.S. Pat. No. 6,461,372 (filed Mar. 8, 2000), each of which is incorporated herein by reference, for more details about this type of structure).

In accordance with an aspect of the subject invention, the instrument 300 is illustratively provided with an optical fiber 312 that includes a plurality of fiber Bragg gratings for sensing shape. Fiber 312 extends through wrist 304 and optionally into some or all of end effector 306. Information about these types of fibers is described in detail in the above-cited patent applications. Other bend sensors could be used. For example, other optical fiber shape sensing technologies that do not require FBGs (e.g., Rayleigh scattering methods) may be used. Magnetic/electric field sensors can be placed along the length of the flexible arm. Alternatively, piezo sensors can be placed at the joints or distributed along body of the arm. Other sensing possibilities include the use of sliding sensing cables that provide position information of joints, or the use of three-dimensional imaging and machine vision approaches to derive instrument position, orientation, and shape. Image-based tool tracking technology may also be used. (See e.g., U.S. Patent Application Publications No. US 2009/0088897 A1 (filed Sep. 30, 2007), US 2009/0088773 A1 (filed Sep. 30, 2007), and US 2009/0088634, A1 (filed Sep. 30, 2007), each of which is incorporated herein by reference.)

The proximal end of fiber 312 is coupled to fiber strain interrogator/detector unit 314. Unit 314 functions to send light down the fiber and to collect and measure reflected light. As noted above, changes in the shape of the wrist 304 strain the gratings associated with the wrist, which in turn will change the character of the returned light in a manner which can be measured.

The output of unit 314 is supplied to an electronic data processor 316. Processor 316 uses the information to determine both the shape of the arm as well as any external forces applied to the arm as discussed above. The external force information may then be used in a teleoperation loop to output an indication of the forces haptically at a master control device (e.g., finger or hand grip), or to output the force indications to the user in some other way (e.g., using visual, vibro-tactile, etc. methods). (See, U.S. Pat. No. 6,424,885, (filed Aug. 13, 1999) incorporated herein by reference.) The external force information may also be routed in a control loop to a controller 318 that automatically controls one or more of the servomotor actuators to keep instrument 300's arm stationary as the external force is applied to or withdrawn from the arm. The shaft 302 and wrist 304 arm configuration is illustrative of various arm configurations as described above.

Figure 4:
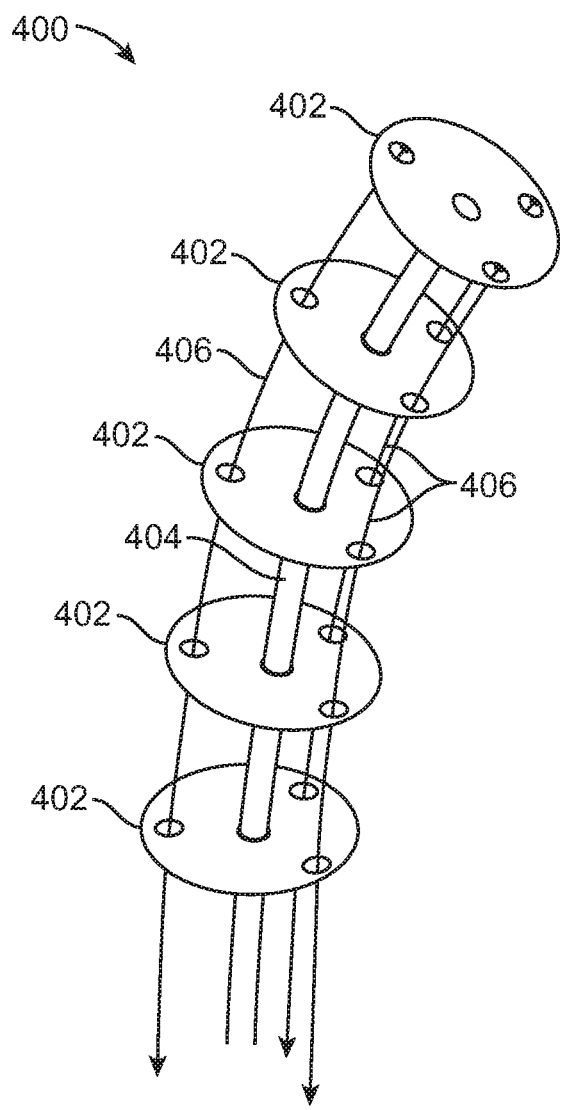
FIG. 4 is diagrammatic view of an articulated arm.

FIG. 4 illustrates another type of robotic arm 400 that could be adapted for use with the subject invention. Arm 400 includes a plurality of spaced apart disks 402. Each of the disks 402 is rigidly attached to a center spine 404. The center spine exerts a spring (stiffening) force that attempts to straighten arm 400 if bent.

Each of three tendons 406 are rigidly attached to the most distal disk 402 and pass through holes in the remaining disks. Arm 400 is not constrained to planar movement, and it is activated by changing the relative tension among the three tendons. In free space, the arm will bend in a smooth arc so as to minimize the energy stored in the center spine. If a force is applied to the arm, however, its shape will change in a manner that can be measured. As with the embodiment of FIG. 3, the embodiment of FIG. 4 is provided with an apparatus as described above for monitoring the change in shape of the arm. One suitable apparatus would be an optical fiber with Bragg gratings, as discussed above.

The ability to recover both the tendon forces and the external forces acting on a movable arm can be used to control the arm. For example, with this information, the control system (FIG. 3) can be programmed to compensate for various drive train dynamics, for example, friction acting on actuation cables.

Referring now to the first illustrative configuration mentioned above (non-actuated continuously flexible arm with a stiffening element), the approach for determining external forces using bend sensors can be applied to flexible probes that contain no actuating mechanisms for internally controlling the motion of the probe. In a simple example, the probe can be a spring element having bend sensors applied thereto. When the distal tip of the probe hits a surface, it will bend into some shape. The bend sensors can be used to determine that shape. The information about the shape can be used to determine the force vector applied to the tip. This concept can apply to a probe within finite degrees of freedom, such as a continuously flexible device or to a device with a finite number of degrees of freedom. An illustrative probe is a whisker-like device that has a known, inherent stiffness.

In the prior art, strain gauges have been mounted on rigid links of an arm to determine some information about lateral forces on the arm that cause shaft bending and shear loads. In the case of the flexible probe discussed above, however, the interest is in deriving bend information that modifies the shape of the probe rather than strain information. Such bend information can be derived using the Luna fiber system mentioned above.

Referring now to the third illustrative condition (actuated discrete link flexible arm without a stiffening element), the subject invention can also be used with robotic arms that are fully actuated with no explicit stiffening elements. Information about external forces can be derived by using the bend sensors to determine how the links deflect (since the links will, in fact, have finite stiffness). In this system, the bend sensor information from the links is used to determine force, and the bend sensor information from the joints is used to determine joint position. Both force and joint position information are usable in a control system, as illustrated above.

In another aspect it can be seen that a similar approach may be used for sensing twist force around a longitudinal axis (i.e., the axis between proximal and distal ends) of an arm. The combination of an optical fiber that is used to sense twist (e.g., a four core fiber with one core aligned with the fiber's longitudinal axis and the other three cores equidistantly spaced around the center core) and a torsion spring that seeks a minimum torsional energy state may be used to determine torque on the linkage arm or continuously flexible arm. The torque sensing multicore fiber may also be used to sense bend, and also lateral force, as described above.

While the subject invention has been described with reference to several embodiments, various changes and modifications could be made therein, by one skilled in the art, without varying from the scope and spirit of the subject invention as defined by the appended claims. Principles and elements illustrated in one or more of the drawings or described above in relation to one aspect, embodiment, or implementation of the invention are not limited solely to that one aspect, embodiment, or implementation, but may be incorporated in various other aspects, embodiments, and implementations. For example, shape sensor apparatus components and electronic data processors that receive information extracted from shape sensor apparatus components may be incorporated as necessary in the various aspects, embodiments, and implementations illustrated and described herein.

What is claimed is:

1. A robotic surgical system comprising:
  a surgical instrument, wherein the surgical instrument includes:
    an elongate, hollow shaft having a proximal end, a distal end, and a flexible section; and
    a sensor apparatus comprising an electromagnetic sensor;
  a force transmission mechanism coupled to the proximal end of the shaft; and
  a processor communicatively coupled to at least the sensor apparatus, wherein the processor is configured to receive sensor data from the sensor apparatus and to use the sensor data with mechanical property data for the surgical instrument and material property data for the surgical instrument to determine external force information for the surgical instrument.

2. The robotic surgical system of claim 1, wherein the processor is further configured to receive three-dimensional imaging data for tracking the surgical instrument.

3. The robotic surgical system of claim 1, wherein the processor is further configured to use the received sensor data, the mechanical property data for the surgical instrument, and the material property data for the surgical instrument to determine internal force information for the surgical instrument.

4. The robotic surgical system of claim 1 wherein the external force information includes information about at least one of a magnitude or a direction of an external force applied to the surgical instrument.

5. The robotic surgical system of claim 1 wherein the sensor apparatus further comprises an optical fiber shape sensor.

6. The robotic surgical system of claim 1 wherein the sensor apparatus further comprises a piezo sensor.

7. The robotic surgical system of claim 1 wherein the surgical instrument further includes a passive stiffening element coupled to the distal end of the shaft.

8. The robotic surgical system of claim 7 wherein the passive stiffening element includes an internal spring.

9. The robotic surgical system of claim 1 wherein the processor is further configured to output an indication to a user.

10. The robotic surgical system of claim 9 wherein the output indication provides a haptic force at a control device.

11. The robotic surgical system of claim 9 wherein the output indication provides a visual cue at a control device.

12. The robotic surgical system of claim 9, wherein the output indication is a visual indicator.

13. The robotic surgical system of claim 1 wherein the processor is further configured to output the external force information in a control loop for receipt by an actuation mechanism for actuating the surgical instrument.

14. The robotic surgical system of claim 13 further comprising the actuation mechanism.

15. The robotic surgical system of claim 1 wherein the flexible section is continuously flexible.

16. The robotic surgical system of claim 1 wherein the mechanical property data includes dimensional information for the surgical instrument.

17. The robotic surgical system of claim 1 wherein the material property data includes friction information.

18. The robotic surgical system of claim 1 wherein the material property data includes stretch property information for a cable actuated by the force transmission mechanism.

19. The robotic surgical system of claim 1 wherein the surgical instrument further includes an end effector at the distal end.

20. The robotic surgical system of claim 1, wherein the processor is further configured to use image based tracking to determine position and orientation information for the surgical instrument.

21. The robotic surgical system of claim 1, wherein the processor is further configured to use image based tracking to determine a shape of the surgical instrument.

* * * * *